United States Patent [19]
Fetner et al.

[11] Patent Number: 5,443,734
[45] Date of Patent: Aug. 22, 1995

[54] PROGRAMMABLE SOLID PHASE EXTRACTION AND ELUTION DEVICE

[75] Inventors: Martin J. Fetner; Elwood F. Seasholtz, both of Allentown, Pa.

[73] Assignee: Applied Separations, Inc., Allentown, Pa.

[21] Appl. No.: 101,784

[22] Filed: Aug. 3, 1993

Related U.S. Application Data

[63] Continuation of Ser. No. 788,578, Nov. 6, 1991, abandoned, which is a continuation-in-part of Ser. No. 488,306, Mar. 5, 1990, abandoned.

[51] Int. Cl.⁶ .............................. B01D 15/08
[52] U.S. Cl. .................... 210/656; 210/142; 210/198.2
[58] Field of Search ............ 210/101, 102, 134, 142, 210/198.2, 264, 656, 659, 143

[56] References Cited

U.S. PATENT DOCUMENTS

| | | | |
|---|---|---|---|
| 3,373,872 | 3/1968 | Hrdina | 210/198.2 |
| 3,504,799 | 4/1970 | Ogle | 210/198.2 |
| 3,508,880 | 4/1970 | Hrdina | 210/198.2 |
| 3,583,230 | 6/1971 | Patterson | 210/198.2 |
| 3,630,371 | 12/1971 | Hrdina | 210/198.2 |
| 3,701,609 | 10/1972 | Bailey | 210/198.2 |
| 3,912,595 | 10/1975 | Philipp | 210/198.2 |
| 3,922,223 | 11/1975 | Burkhartsmeier | 210/198.2 |
| 3,923,460 | 12/1975 | Parrott | 210/659 |
| 3,925,207 | 12/1975 | Scriba | 210/198.2 |
| 3,954,617 | 5/1976 | Ishimatsu | 210/198.2 |
| 3,963,614 | 6/1976 | Ozawa | 210/198.2 |
| 3,966,410 | 6/1976 | Jahnsen | 210/198.2 |
| 4,042,499 | 8/1977 | Ramstad | 210/659 |
| 4,102,610 | 7/1978 | Taboada | 417/417 |
| 4,116,046 | 9/1978 | Stein | 210/198.2 |
| 4,154,583 | 5/1979 | Favre | 210/198.2 |
| 4,158,630 | 6/1979 | Stearns | 210/198.2 |
| 4,271,697 | 6/1981 | Mowery | 210/198.2 |
| 4,274,967 | 6/1981 | Snyder | 210/198.2 |
| 4,333,498 | 6/1982 | Huling | 137/625.64 |
| 4,364,263 | 12/1982 | Sankoorikal | 210/198.2 |
| 4,448,684 | 5/1984 | Paradis | 210/198.2 |
| 4,478,713 | 10/1984 | Girot | 210/198.2 |
| 4,500,432 | 2/1985 | Poole | 210/659 |
| 4,501,297 | 2/1985 | Baker | 137/625.46 |
| 4,645,489 | 2/1987 | Krumme | 251/11 |
| 4,746,490 | 5/1988 | Saneii | 436/161 |
| 4,766,082 | 8/1988 | D'Autry | 210/198.2 |
| 4,767,279 | 8/1988 | Dourdeville | 210/198.2 |
| 4,840,730 | 6/1989 | Saxena | 210/198.2 |
| 4,900,446 | 2/1990 | Anderson | 210/198.2 |
| 4,954,253 | 9/1990 | Alexandrov | 210/198.2 |
| 4,960,516 | 10/1990 | Alexandrov | 210/198.2 |
| 4,969,993 | 11/1990 | Nash | 210/198.2 |
| 5,087,369 | 2/1992 | Tanimoto | 210/198.2 |
| 5,091,092 | 2/1992 | Newhouse | 210/198.2 |
| 5,100,557 | 3/1992 | Nogami | 210/198.2 |
| 5,107,908 | 4/1992 | Newhouse | 210/198.2 |

*Primary Examiner*—Ernest G. Therkorn
*Attorney, Agent, or Firm*—Sanford J. Piltch

[57] ABSTRACT

An automated, integrated system for programmably selectively extracting and purifying one or more particular solutes from a contaminated solution, said purified solutes then being recovered as a concentrated solution suitable for analysis.

12 Claims, 10 Drawing Sheets

SPE-ED WIZ
PROCEDURE REPORT

PROCEDURE NAME : TEST PROCEDURE #1
RUN BY : PILTCH
DATE : Tue, Aug 13, 1991
START TIME : 10:52:51
STOP TIME : 10:54:05
RUN # : 912241050

---

HARDWARE STATUS : Spe-ed Wiz IS NOT connected.
FIRST CARTRIDGE : 1
LAST CARTRIDGE : 10
BLOW-DOWN TIME : 0 seconds
PUMP CYC WASTED : 2 cycles
CARTRIDGE TYPE : 2001
CARTRIDGE DESC : C 1B

---

Cartridge Serial Numbers 1  54155465426
2  156547
3  145466867
4  9454279
5  54377980

6  347567957543
7  45746790
8  679
9  54869867
10 769

---

| CYCLE Number | Solution Name | Volume (ml) | Aliq. | Flow Rate | High Time | Dry Time | Pause? |
|---|---|---|---|---|---|---|---|
| Cond. # 1 Dispenensed: | METHANOL 2 | 01.0 | 1 | 24 | 2.0 | 1.0 | N |
| Cond. # 2 Dispensed: | WATER 2 | 01.0 | 1 | 10 | 0 | 0 | N |
| Message : | add 2ml of serum. | | | | | | |

Sample Dry Time : 5

| Wash #1 Dispensed: | WATER 2 | 00.6 | 2 | 12 | 03 | 04 | N |
|---|---|---|---|---|---|---|---|
| Message : | place collection tubes in the manifold | | | | | | |
| Elut. #1 Dispensed: | NAOH 2 | 12.6 | 1 | 10 | 1 | 10 | Y |
| Message : | code samples before removing. | | | | | | |

---

Solution Usage Summary

1  METHANOL          1.0    # 3  NAOH          12.6
2  WATER             1.6

FIG. 8

```
┌─────────────────────────┐
│ Spe-ed Wiz II Main Menu │
└─────────────────────────┘
┌─────────────────────────┐
│ Run a Procedure         │
│ Create/Edit a Procedure │
│ Methods Development     │
│ Change Report Parameters│
│ Change Report Options   │
│ Quit                    │
└─────────────────────────┘

┌──────────────────────┐
            │ Revision 1.70 08/05/91│
            └──────────────────────┘
```

| | Solution | Vol | Aliq | Flow | Hold | Dry | P |
|---|---|---|---|---|---|---|---|
| Title: TEST PROCEDURE #1 | | | | | | | |
| Cartridge Type: 2001 | Cartridge Descriptor: C 18 | | | | | | |
| | Solution Name | Vol (ml) | Aliq | Flow Rate (ml/min) | Hold Time (sec) | Dry Time (sec) | P |
| Conditioning: | METHANOL | 01.0 | 1 | 24 | 2.0 | 1.0 | N |
| Conditioning: | WATER | 01.0 | 1 | 10 | 0 | 0 | N |
| Conditioning: | | 00.0 | 1 | 2 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |
| Conditioning: | | 00.0 | 1 | 0 | 0 | 0 | N |

Ctrl-Left(Right) — Previous(Next) Field: Up(Down) — Previous(Next) Line
<ESC>—Abort edit F10-Exit and Save

FIG. 9a

```
                        Solution           Vol  Aliq  Flow   Hold   Dry   P
Condition Message: add 2ml of serum.
Sample Dry Time (sec): 05
                   Solution        Vol  Aliq  Flow   Hold   Dry   P
                   Name                       Rate   Time   Time
                                   (ml)       (ml/min)(sec) (sec)
Wash:    WATER                     00.6  2    12     03     04    N
Wash:                              00.0  1    0      0      0     N
Wash:                              00.0  1    0      0      0     N
Wash:                              00.0  1    0      0      0     N
Wash:                              00.0  1    0      0      0     N
Wash:                              00.0  1    0      0      0     N
Wash:                              00.0  1    0      0      0     N
Wash:                              00.0  1    0      0      0     N
Wash:                              00.0  1    0      0      0     N
```

Ctrl-Left(Right) — Previous (Next) Field: Up(Down) — Previous(Next) Line
<ESC>—Abort edit  F10—Exit and Save

FIG. 9b

```
                        Solution           Vol  Aliq  Flow   Hold   Dry   P
Wash:                              00.0  1    0      0      0     N
Wash:                              00.0  1    0      0      0     N
Wash:                              00.0  1    0      0      0     N
```

Wash Message: place collection tubes in the manifold

```
                   Solution        Vol  Aliq  Flow   Hold   Dry   P
                   Name                       Rate   Time   Time
                                   (ml)       (ml/min)(sec) (sec)
Elution:  NAOH                     12.6  1    10     1      10    Y
Elution:                           00.0  1    0      0      0     N
Elution:                           00.0  1    0      0      0     N
Elution:                           00.0  1    0      0      0     N
Elution:                           00.0  1    0      0      0     N
Elution:                           00.0  1    0      0      0     N
Elution:                           00.0  1    0      0      0     N
Elution:                           00.0  1    0      0      0     N
```

Ctrl-Left(Right) — Previous (Next) Field: Up(Down) — Previous(Next) Line
<ESC>—Abort edit  F10—Exit and Save

FIG. 9c

|  | Solution | Vol | Aliq | Flow | Hold | Dry | P |
|---|---|---|---|---|---|---|---|
|  | Solution Name | Vol (ml) | Aliq | Flow Rate (ml/min) | Hold Time (sec) | Dry Time (sec) | P |
| Elution: | NAOH | 12.6 | 1 | 10 | 1 | 10 | Y |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |
| Elution: |  | 00.0 | 1 | 0 | 0 | 0 | N |

Elution Message:     code samples before removing

Ctrl-Left(Right) — Previous (Next) Field: Up(Down) — Previous(Next) Line
<ESC>—Abort edit  F10—Exit and Save

Set Procedure Parameters

First Cartridge   1          Last Cartridge   30

|  | Value Position |
|---|---|
| METHANOL | 1 |
| WATER | 2 |
| NAOH | 3 |

Ctrl-Left(Right) — Previous(Next) Field
Up(Down) — Previous(Next) Line
ESC—Abort edit  F10—Exit and Run

PROGRAMMABLE SOLID PHASE EXTRACTION AND ELUTION DEVICE

CROSS-REFERENCE TO RELATED APPLICATION

This application is a continuation of U.S. patent application Ser. No. 07/788,578, filed Nov. 6, 1991, which is a continuation-in-part of U.S. patent application Ser. No. 07/488,306, filed Mar. 5, 1990, both now abandoned.

FIELD OF THE INVENTION

The present invention relates to devices adapted to process a liquid having one or more solutes dissolved therein by causing said liquid to contact a solid extractant or sorbent to remove said solutes and more particularly to programmable systems adapted to meter a preselected amount of said liquid from a selected storage container and transfer said metered liquid to one or more programmably selectable receptacles containing said solid sorbent for said solute removal and the concentration of said removed solute for subsequent recovery.

BACKGROUND OF THE INVENTION

Liquid/liquid extraction is a laboratory and industrial technique for separating a dissolved solute from a solution thereof which has been in use for many years. Such method comprises one or more steps in which a first liquid solution of a solute in a first, relatively nonvolatile, solvent is vigorously mixed with a second, usually organic, solvent. The second solvent, while having a high affinity for the solute material, is both much more volatile than the first solvent and substantially immiscible therewith. Recovery of the solute is accomplished by separating the two liquids and then evaporating the second solvent to allow the recovery of the solute therefrom. Such method, while relatively simple to perform, suffers from the disadvantage that the most suitable volatile solvents are materials such as hexane, benzene, ether, acetone, methyl chloride, acetonitrile and chloroform. All of these materials present substantial flammable and/or toxic hazards so that proper handling and recovery constitutes an ever more stringent set of environmental and economic problems. In extreme cases, the costs of disposing of these materials can be anywhere from 5 to 10 times the initial cost of the organic solvent. Further, when such an approach is used, for example, in the testing of urine or blood samples for one or more drugs, the relatively long times required for such an extraction causes serious problems in many high-volume analytical laboratories. With all of this, it has been reported that, as recently as 1984, of the 400 million plus analytical samples prepared and tested in the nation's biological, clinical, pharmaceutical, toxicological, forensic, environmental, chemical, food and cosmetic laboratories, over 60 percent were still prepared by liquid/liquid extraction.

One emerging technology being used to overcome these problems is known as solid phase extraction. Using this method, the first solution containing solvent is passed through a cartridge containing a selected solid inorganic or organic sorbent phase to extract the solute from the solvent. One typical sorbent material for this purpose is an ion exchange resin which removes dissolved salts of calcium, iron and similar mineral material from water in many household and industrial water softener units. In many cases, the desired product is usually the "softened" water. In these units the resin is rejuvenated by periodically backflushing the resin bed with a salt solution and discarding the flush solution to a public sewer. In other cases, the extracted mineral material is of interest, and the backflush solution is retained in the system to recover the dissolved solute. While many large units based on this technique can be found in industry, there has not been a concomitant development of special, relatively small, automated units utilizing this approach to meet the needs of forensic, toxicology, clinical and other high volume analytical laboratories.

SUMMARY OF THE INVENTION

The present invention comprises an automated, integrated programmable system which provides for use of a solid sorbent to accomplish the rapid extraction and concentration of organic and/or inorganic solutes from dilute solutions thereof and then the recovery of said concentrated solute for analysis or other use. As used herein the terms "programmably" or "programmable" mean an operation conducted under the control of a computer or controller. In the present invention, the sorbent is a solid phase material, such as an organic resin, which is selected as being especially suitable for removing the dissolved solute of interest. Further, all operations relating to the processing of the fluids, from the initial conditioning of the sorbent in cartridge receiver tubes, the placing of the raw materials in the receiver tubes, the metering of the treatment fluids from one or more solution containers to one or more selected cartridge receiver tubes, to the final elution and removal of the concentrated solute from one or more selected cartridge receiver tubes are performed in a fully integrated system in which all process steps are performed under the instructions delivered from a central programmable controller or computer. The system is further adapted to process a plurality of raw input solutions and to provide a multiplicity of output concentrates of one or more extracted solutes from these raw solutions. Such capability is made possible by the incorporation of special multi-port valves which are adapted to allow the transfer of all solutions, as set up in the controller, from selected one(s) of the solution/solvent containers to selected one(s) of the receiver tubes. In use, such a system is found to be over ten times faster and costing only about 1/10th as much as conventional liquid/liquid extraction. Further, the quantities of materials subject to one or more environmental controls can be considerably reduced.

BRIEF DESCRIPTION OF THE DRAWINGS

For the purpose of illustrating the invention, there is shown in the drawings forms which are presently preferred; it being understood, however, that the invention is not limited to the precise arrangements and instrumentalities shown.

FIG. 8 is a monitor display screen for a test run to be performed by the embodiment of FIG. 7.

FIGS. 9a to 9d illustrate process status display screens as generated by the test run in the embodiment of FIG. 7.

FIG. 10 is a display screen showing the sample locations for the test solutions used in the test run illustrated in FIG. 8.

DETAILED DESCRIPTION OF THE INVENTION

The following detailed description is of the best presently contemplated modes of carrying out the present invention. This description is not intended in a limiting sense, but is made solely for the purpose of illustrating the general principals of the invention.

Figure 1:
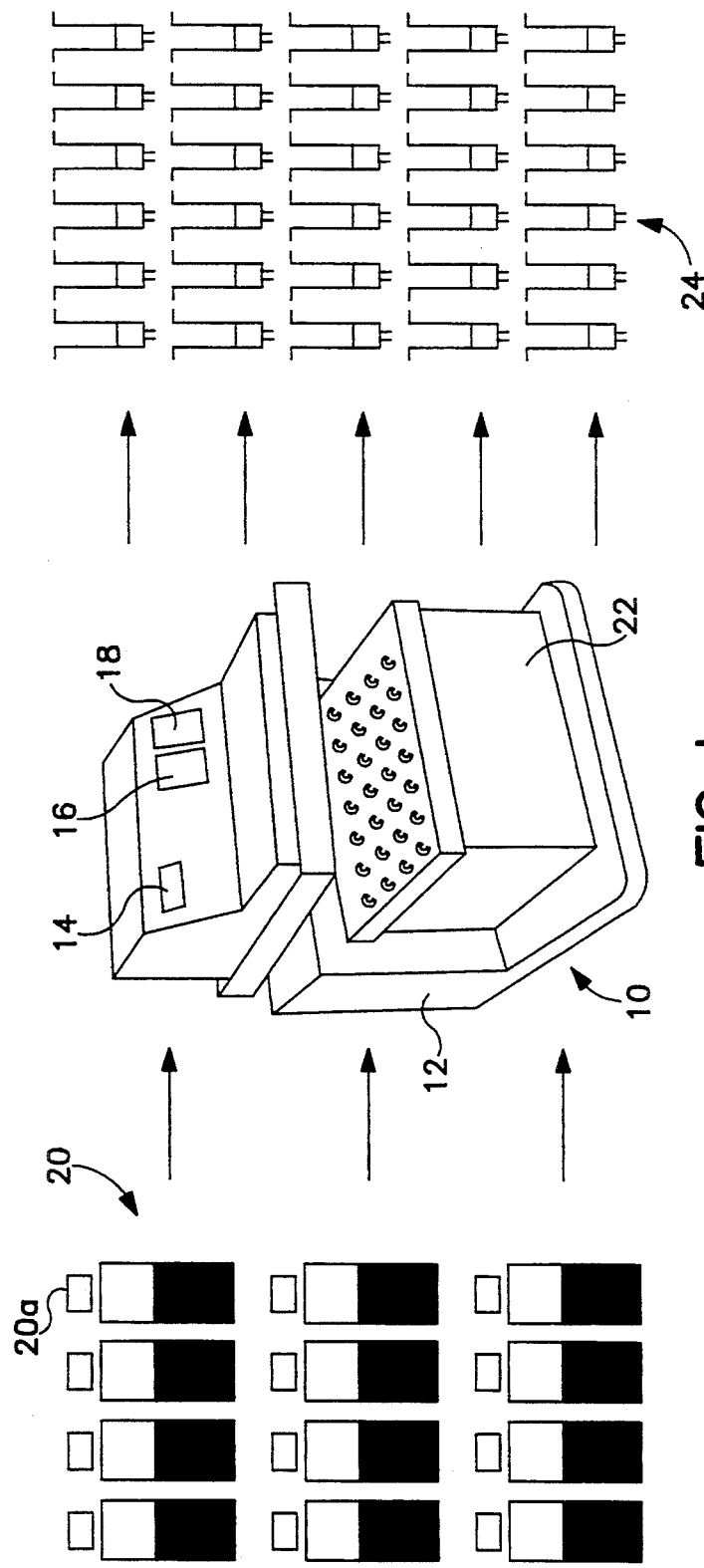
FIG. 1 is a simplified diagrammatic representation showing the principal external features of the present invention.

Referring now to the drawings in detail, wherein like numbers represent like elements, there is shown in FIG. 1 the principal external features of the system of the present invention in a simplified diagrammatic representation of the basic flow path of fluid materials therethrough. In the center is process unit 10 which contains, within housing 12, all of the individual units, along with their associated electrical and plumbing connections, which are used to meter and control the flow of fluids into, through, and out of the system. On the front of the upper projection of housing 12 is an alpha-numeric display 14, number keypad 16 and function select keypad 18, the functions of which will be explained below. In the embodiment illustrated, process unit 10 is adapted to receive treatment solutions of desired fluids from a plurality of solution containers (for the purpose of this illustration the number of solution containers or receptacles is 12), collectively 20. Also shown is stand 22 which, as shown, is adapted to support, position, and retain a plurality of cartridge receiver tubes, collectively 24, firmly in place under the outlet taps (not shown) within the confines of the process unit 10. Also within the confines of stand 22 is an outlet adapted to receive discharged fluids and convey them either to a waste storage receptacle (not shown) or to a series of eluted sample containers (also not shown) corresponding in number and placement to the receiver tubes.

In the particular embodiment shown, the containers 20 are used to supply both the raw fluid material (such as contaminated water, blood or urine) from which a solute is to be extracted and one or more solvents and wash solutions used in the resulting process. These solvents and wash solutions are used to remove any contaminants, such as residual raw solution adhering to the extracted solute and/or achieving the final elution and concentration of the solute after it has been extracted from the raw solution. Suitable solvents and wash solution materials include water, methanol, acetonitrile, ethyl acetate, chloroform, toluene, hexane, and dilute NaOH, saline and acid solutions. When the test material is a fluid, the upper segment of the process unit 10 (which overhangs the stand 22) is pivoted upward and one or more aliquot samples of the raw test material or fluid is pippetted into selected ones of the cartridge receiver tubes 24. Prior to such placing of the raw test fluid in the cartridge receiver tubes 24, one or more of the solutions stored within containers 20 may be used to pretreat or condition the sorbent material in the selected receiver tubes 24. Thereafter, the system operating procedure is configured to cause aliquot portions of the same and other solutions to be metered from the containers 20 for further processing at the appropriate times.

Although the described embodiment can cause containers 20 to automatically supply the fluid raw materials or samples to the receiver tubes 24, manually introducing the raw fluid material offers several advantages. For example, this procedure does not present any potential problems with contaminating the system fluid lines and connections. This approach allows the introduction of the raw fluid samples into as many as thirty (30) cartridge receiver tubes 24 by having the system operator pippette requisite aliquot portions of the samples directly into the receiver tubes 24 after they have been conditioned with one or more solvents. This manual introduction of the samples also permits a greater number of containers to be used for storage of a larger variety of treatment solutions and solvents for use in extracting the solutes from a variety of sample solutions and materials.

Moreover, the system is not limited to processing liquid sample solutions. Solid materials, if properly shredded or granulated may also be processed. These materials can be processed merely by first placing a weighed amount of the solid material into each of the cartridge receiver tubes 24 being used (after appropriate conditioning), repositioning the upper segment of the process unit 10 over stand 22, and then adjusting the process schedule to achieve the desired results.

In the embodiment illustrated, the processing of the sampled solution(s) can be conducted, simultaneously, in as many as thirty (30) of the cartridge receiver tubes 24. Here too, it should be appreciated that facilities able to accommodate larger or smaller numbers of sampling containers 20 or cartridge receiver tubes 24 may be used without affecting the scope of the present invention.

Entering into the rear of housing 12 is the inlet tube 26 for a gas supply (not shown), the purpose of which will be explained below. Also not shown are a plurality of inert, preferably Teflon, hollow fluid transfer tubes, one coming from each of sample containers 20 to selectively provide a fluid flowpath into the other operating components of the system being presently described. These fluid transfer tubes may be of any convenient size necessary to transport the solutions and solvents to the process unit 10.

Figure 2:
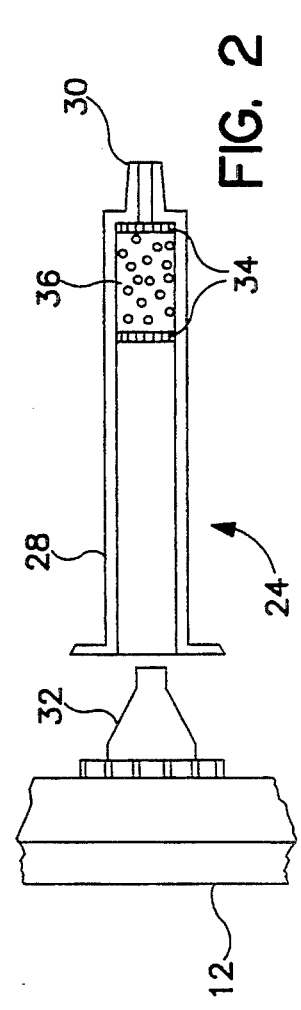
FIG. 2 is a plan view of an extractant receiver tube and extractant cartridge used in the present invention.

Referring to FIG. 2 each of the cartridge receiver tubes 24 comprises a body 28, which is also made from an inert material. In performing the processes of the present invention it is critical that sample integrity not be compromised by any contamination leaching out from the body 28 when contacted by one or more of the solvents, rinses and other materials being used. While many nominally "inert" materials may be used to make the bodies 28, it has been found that Teflon and polypropylene are the least sensitive to the various rinses, solvents, and other materials used, and are preferred.

Cartridge receiver tube 24 is open at the top, while at the bottom is an outlet nozzle 30 having a very small orifice therein to permit the solute or other fluids used to drain therefrom for subsequent collection, disposal and/or final processing or analysis.

Inside the distal or bottom end of cartridge receiver tube 24 are a separated pair of inert packing frits 34, mounted across the width of the cartridge receiver tube body 28, between which a predetermined portion of a selected solid extractant or sorbent material 36 is retained. The solid sorbent 36 used is selected specifically to remove one or more particular solutes from a given solution, so a different extractant must be used when different solvent/solute samples are involved. Typical solid sorbents useful in the present invention are alumina (neutral, acidic or basic), silica gel, benzosulfonic acid, and one or more ion exchange resins such as the Amberlite resins obtainable from the Rohm and Haas Co. In the embodiment illustrated, changing tubes to meet particular requirements is both simple and relatively inexpensive. Preloaded cartridge receivers according to the above description can be obtained from Applied Separations, Inc. of Allentown, Pa. Cartridges currently available range from a sorbent volume of about 1 ml to about 12 ml with the sorbent quantity ranging from about 100 to about 1000 mg. The particular one(s) chosen would depend on such factors as the volume of raw fluid involved and the type and concentration of the solute dissolved therein.

When the various cartridge receiver tubes 24 are mounted within the stand 22 and positioned within the processing unit 10 they are effectively aligned in positions beneath corresponding outlet nozzles 32 of standard Luer slip fitting configuration. These nozzles 32 are mounted to the underside of the upper housing extension 12 and fit into the open top of each corresponding receiving tube 24 mounted within the stand 22. The design serves to close off the relatively large top of body 28 and provide a pressurized seal which allows the fluids to be forced through the cartridge receiver tubes 24 when gas pressure is applied. The seal also provides against airborne or liquid contamination from entering the receiver tubes 24.

Internally, attached to each of these outlet nozzles 32 is a related binary position (on/off) valve (not shown) through which the various solutions used are introduced into the receiver tubes 24. Also associated with each of outlet nozzles 32 is a pressure sensing means (also not shown) for sensing the presence or absence of a receiver cartridge 24 at a particular position within stand 22 whenever the system is placed in operation. The normal operating position of this valve is "off" or closed. The valve opens or is "on" only when the pressure sensing means determines there is a cartridge receiver tube 24 at that position. Where no cartridge receiver tube 24 is present, the binary position valve remains in the "off" position so it is not possible to pass any fluids therethrough, even if the system is programmed to do so. This effectively protects the system and overall work place environment from unintended discharges into the working area if there is no cartridge receiver tube 24 at a programmed position in the system.

As noted above, reaction time within the cartridge receiver tubes 24 and the subsequent discharge of the reactant fluids through outlet nozzle 30 is controlled by the ability of the sorbent material to pass the fluid and by a positive gas pressure generated by the process unit 10. Fluids are retained within the receiver tubes by the hydrophobic property of the sorbent and do not flow through the receiver tubes entirely until a positive gas pressure is applied through outlet nozzle 32. Thus, whenever it is required to establish that a certain amount of contact time occurs to accomplish the particular wash or dissolution operation underway in the program cycle, positive gas pressure is withheld. A more complete explanation of the positive gas pressure, and the method of application and removal follows below. It should be understood that in a totally automated system, all aspects of the system including the generation of a positive gas pressure and routing of the input and discharged fluids would be controlled as a part of the overall system operation.

Figure 3A:
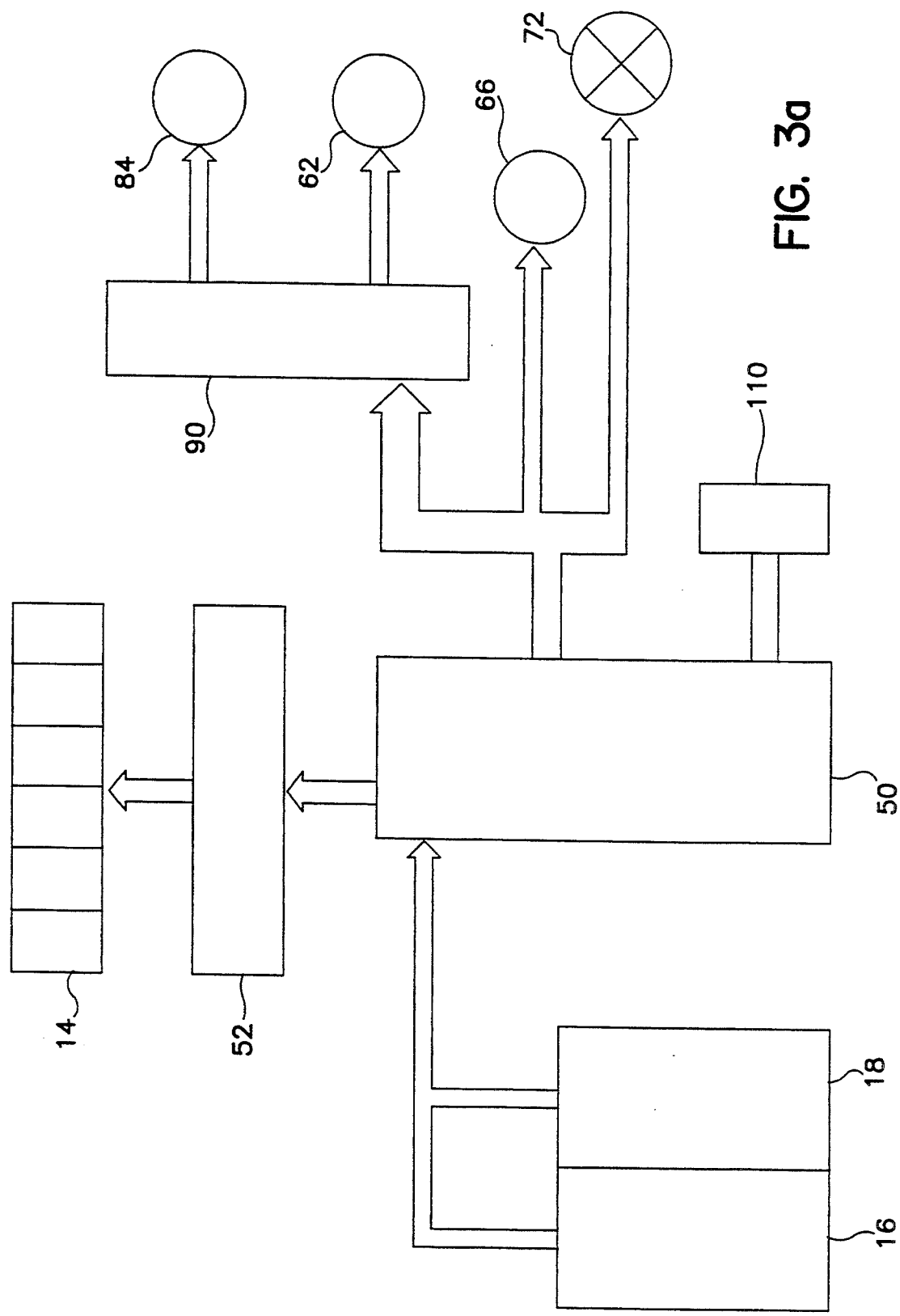
FIGS. 3a and 3b are schematic diagrams showing the general electrical and mechanical relationships, respectively, of the principal elements of the present invention.
Figure 3B:
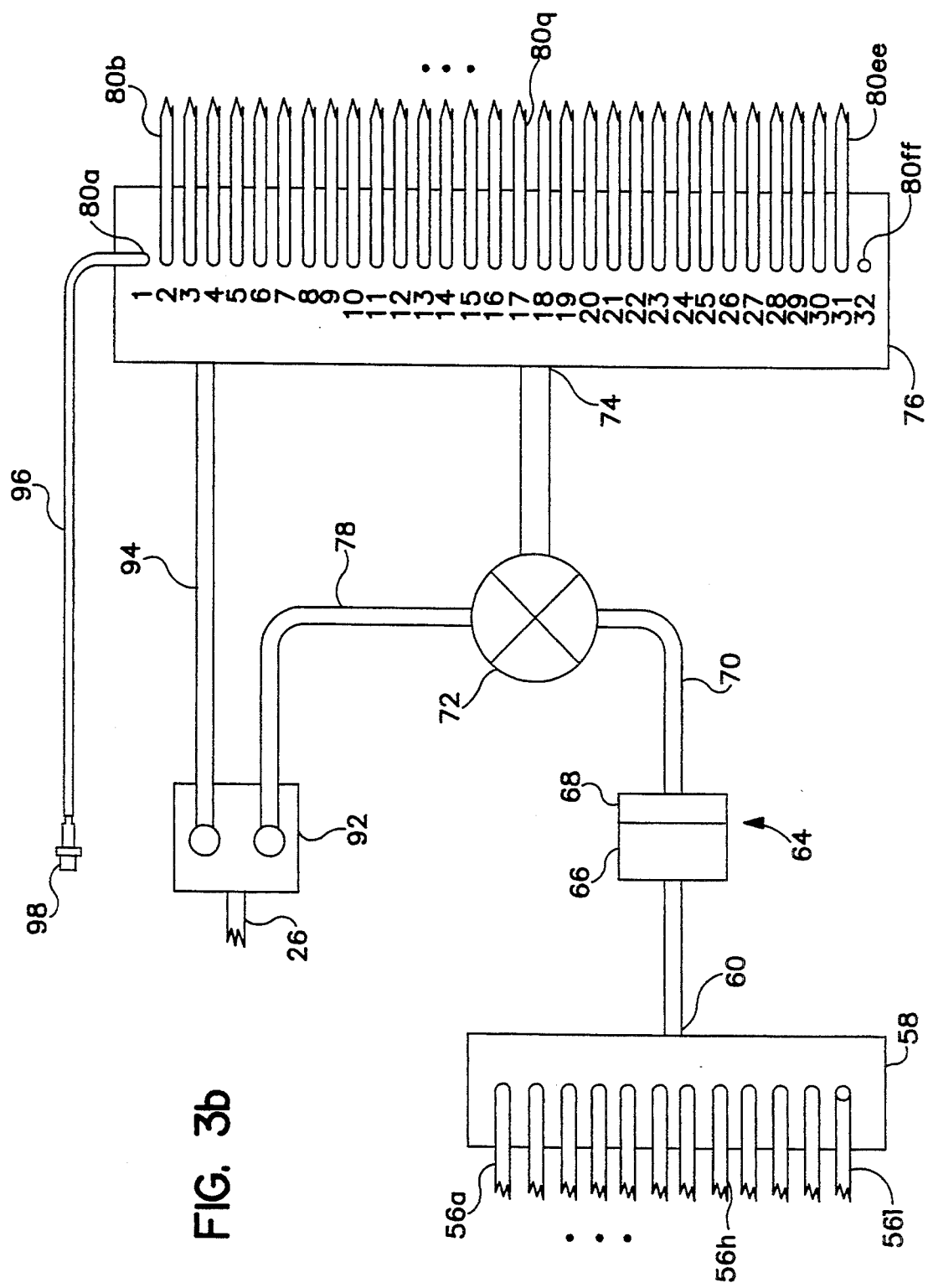

The internal electrical and mechanical configurations of the process unit 10 are shown as FIGS. 3a and 3b, respectively. Central to the operation of process unit 10 is the programmable controller 50 which is adapted to receive and act upon numerical and functional directions entered from keypads 16 and 18, as shown in FIG. 3a. Typically, keypad 16 is a standard 10 key unit used to enter numerical selections of both the sample containers 20 and the cartridge receiver tubes 24. The function keypad 18 is used to select operating cycles for a particular operation of the system.

In one embodiment, the user can select one or more of 6 such cycles. For convenience, these have been identified as follows:

(1) the "PROGRAM" cycle, wherein the unit can be directed to dispense the number of aliquot portions of the raw sample solutions (usually, but not necessarily, one) and the rinsing agents which are to be taken from selected sample containers 20 and sent to a preselected group of cartridge receiver tubes 24 for subsequent use;

(2) the "BATCH" cycle which performs selected process operations identically in all of the cartridge receiver tubes 24;

(3) the "RANDOM" cycle which allows the user to specify a particular set of process operations for any or all of the cartridge receiver tubes 24;

(4) the "DRY" cycle wherein a stream of a dry inert gas is applied through outlet nozzle 32 to any or all of cartridge receiver tubes 24 for a selected period of time, with the used gases typically being vented to the outside atmosphere;

(5) the "PURGE" cycle which prepares and clears all process lines for future use; and, (6) the "TEST" cycle wherein the system provides diagnostic means for manually operating each of the individual system components.

It is to be understood that other control systems may be used and while other functions may also be built into the system to accommodate other needs, the six functions described above have been found to be sufficient to allow considerable versatility in the operation of the system to accommodate a wide variety of process problems. All of the information needed by the user to select the mode and scope of operation is presented to him via display driver 52 to alpha-numeric display 14.

It is also understood that other input and output devices, such as a central computer and/or a video display or printer may augment or be substituted for the particular control and display units described above. Regardless of the control and display system used, once the program of operation is selected, the operation continues until all the programmed steps are completed.

Conditioning and process solutions are normally stored in and taken from containers 20. As noted, attached to each of these sample containers is one of a plurality of flexible tubes (not shown) which fit through container cap 20a. These tubes extend essentially to the bottommost portion of said sample containers so as to be able, when required, to draw aliquot portions of the contained fluid therefrom. Each of the tubes is connected at its opposite end to a separate inlet port 56a–56l of a first rotary multi-port valve 58. As shown in FIG. 3b, multi-port valve 58 has a plurality of inlet positions, in this case 12 in number, and a single outlet port 60. The valve 58 is constructed with an internal, rotatable central disk portion in which the inlet ports 56a–l are located in a symmetrical fashion around the periphery or circumference thereof. A selected fluid can only flow through a selected inlet port 56a–l and the outlet port 60 when the central disk is rotated to align the outlet with the selected inlet port. Rotation of the central disk of the first multi-port valve 58 is accomplished with a programmable stepper motor 62, which is set such that an integral number of steps, i.e. 1, 2, 3, etc. forward, as directed by controller 50, will precisely move the central disk from one inlet port position to another, as required by the process. That is, each of individual containers 20 can be individually accessed merely by rotating the central disk portion of the first multi-port valve 58 until the internal connecting passage of the central disk is opposite the selected one of the inlet ports 56a–l, at which time the required fluid, which may be the raw solute/solvent sample, one or more pre- or post-wash solutions, an elution solution, or any other process solution, can be withdrawn from the selected container and started through the desired fluid path.

Fluid movement into and through valve 58 is accomplished with pump assembly 64, which is comprised of solenoid drive 66 and self-priming pump 68. In a preferred embodiment, the solenoid drive and pump are chosen to effectively cooperate in such a manner that the amount of fluid metered into the system from any of the solution containers 20 can be precisely controlled to within rather close tolerances. In this embodiment, such effective cooperation is achieved when drive 66 is a solenoid type drive, capable of receiving and reacting to precise instructions from the controller 50, and self-priming pump 68 is a diaphragm pump. The system is set up so that when a proper fluid path is established through valve 58, operation of the pump system 64 will cause a metered amount of the selected fluid to be withdrawn from the selected one of containers 20 by pump 68 for each pulsed step of solenoid drive 66, with said withdrawn fluid then passing through the open path in valve 58 and diaphragm pump 68 and directed through the remaining segments of the selectable fluid flowpath of the system. Thus, it is the number of times the solenoid drive 66 is pulsed which establishes how much fluid is withdrawn (metered) and used in any particular operation of the system.

As shown in FIG. 3b, in the embodiment illustrated, the output from pump 68 flows through output line 70 into a solenoid controlled 3-way valve assembly 72. The 3-way valve 72 acts as a traffic controller in directing the fluid flow into the correct path after the appropriate connections have been established into and through the system. In a first position of 3-way valve 72, a controlled amount of a selected fluid (solute or solvent) from a selected solution container 20 is passed into the inlet port 74 of a second multi-port valve 76 from the outlet 60 of the first multi-port valve 58. In a second position, a "drying" gas (which may be air or an inert gas such as nitrogen, helium or carbon dioxide) from inlet line 26 and internal connector line 78 can be applied through the central inlet port 74 into the interior of valve 76. This flow of gas acts to propel any fluid remaining in the inlet line 74 of multi-port valve 76 into and through the particular one of outlets 80a–80ff which is open at the time, and then assists in the passage of a solution or solvent through the sorbent material in the corresponding cartridge receiver tube 24. By so doing, the inlet line is cleared of raw, rinse or wash fluids which might otherwise act as contaminants in the next operation and thus "dried." This is especially important if the fluid tends to "wet" the interior walls of the piping in the system and not flow out. While in the second position, it is also possible for the gas pressure to be utilized to discharge residual fluids in the lines through the multi-port valve 76 and out of the unit through a fluid discharge line 96, which is described in greater detail in connection with the operation of valve 76. The particular position of 3-way valve 72 at any point in the process cycle is controlled by the controller 50 according to the specific instructions built into each program cycle.

Figure 4:
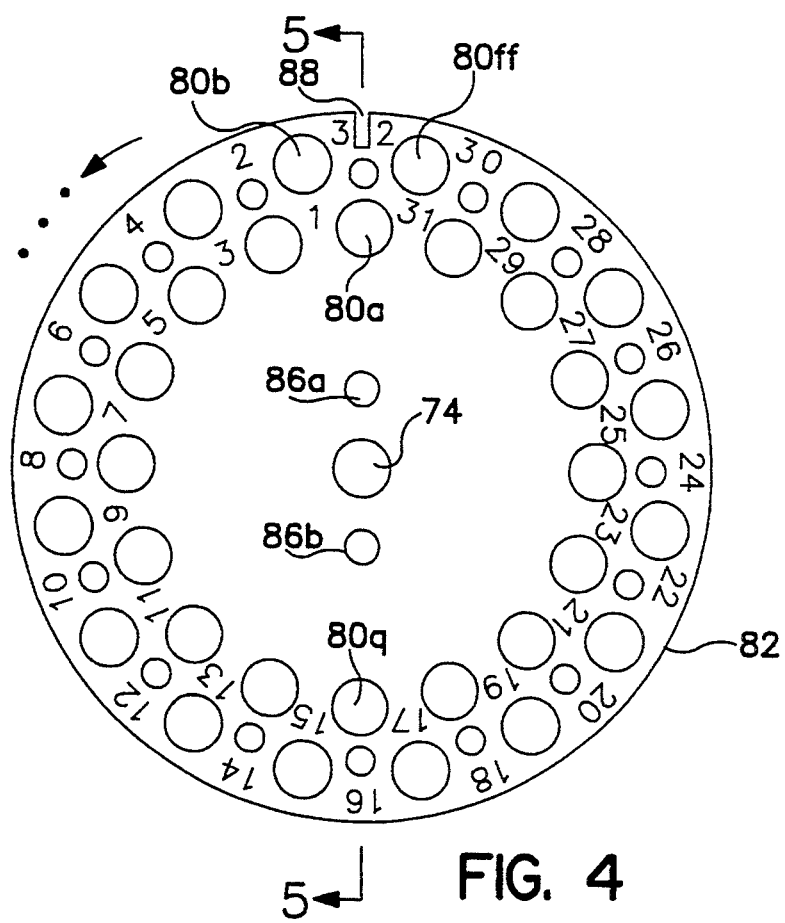
FIG. 4 is a front view of a multi-port valve rotary disk member used in the present invention.
Figure 5:
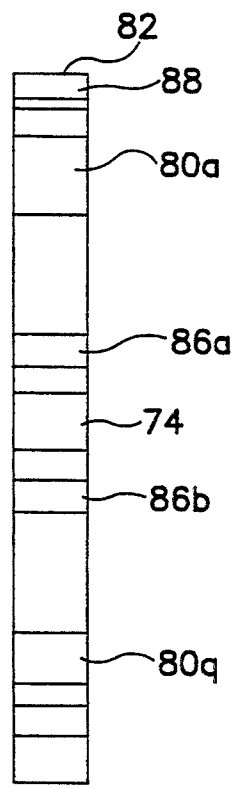
FIG. 5 is a sectional view of the multi-port valve rotary disk member taken along line 5—5 of FIG. 4.

Referring now to FIGS. 4 and 5, the central portion of a 32 position multi-port valve 76 is shown. This valve is the reverse of multi-port valve 58 in that it has but a single inlet port 74, which receives the output of pump 68, and a plurality of outlet ports 80a–ff. It should be noted that output port 80a is normally attached to a discharge line, the purpose of which will be explained below and that output port 80ff is typically without connection to facilitate a rest or null position. As shown, the outlet ports 80a–ff are located about the periphery of a rotatable disk 82 and are arranged in two concentric circles around the circumference thereof. As disclosed above, the fluid discharged from each of these outlet ports goes into a predetermined one of cartridge receiver tubes 24 through the associated outlet nozzles 32. The rotatable disk 82 and, more particularly, the rotatable inlet port 74 and respective outlet port apertures 80a–ff located on the disk 82 are maintained in close juxtaposition to the other by a gas balancing pressure to be described more fully below. Positioning of the inlet port 74 internal aperture relative to each of the outlet ports 80a–ff in valve 76 is controlled by a programmable stepper motor 84.

A different fluid path between the single inlet port 74 and the outlet ports is established each time the stepper motor 84 is moved forward by the controller. The stepper motor 84 controls the movement of central disk 82 by attachment of the disk 82 through holes 86a, b to the stepper motor 84. The inlet and outlet port apertures are accurately aligned through the use of a photo-illumination/detection pair, operably connected through the disk 82 at alignment hole or slot 88, and the stepper motor 84. It will be this signal, the completion of the photo-illumination and detection link, which indicates the initial position of the disk 82, i.e. a "home" or rest position. Then the controller 50 calculates the number of steps required to reach the desired outlet port and sends the "count" to the signal interpreter 90 with instructions for the programmable stepper motor 84. The motor 84 is then energized and counts the number of steps required for the disk 82 to reach the requested outlet port 80a–ff.

Alternatively, another disk may be placed on the central shaft of the stepper motor 84 having a slot located along its circumference, which slot is disposed perpendicularly to the point on the circumference. The photo-illumination/detection pair can be placed in fixed position on either side of this disk with the slot serving the identical purpose as the slot 88 described in connection with disk 82, to create a position sensing apparatus which indicates a "home" or rest position. Counting by the controller 50 from the rest position and instructing the stepper motor 84 with a specific "count" to rotate the disk 82 to align the inlet port 74 with the desired outlet port is then efficiently accomplished.

The discussion above regarding multi-port valve 76 also applies, generally, to the internal structure of valve 58. Typically, all the actions of both valve motors 62 and 84 are controlled directly by signal interpreter 90 according to the instructions received from system controller 50.

Returning to the 3-way valve 72, as shown in FIG. 3b, gas line 78 is connected at its far end to manifold 92. Typically the gas enters the manifold with a pressure of about 25 psi. The outlet pressure into line 78 is reduced therein to about 5–7 psi. It is this gas pressure which acts as the "blow-down" agent propelling and assisting any fluid remaining in the line into the selected cartridge receiver tube 24. The manifold 92 also applies a gas balancing pressure of about 8–10 psi, provided through line 94, to a chamber behind the rotatable disk 82. This balancing pressure acts as an air spring to force the rotatable disk 82 against the opposed stationary portion of the multi-port valve 76, maintaining the inlet port against, or in close juxtaposition to, the moveable outlet ports arrayed about the disk 82.

At certain times a positive gas pressure is applied to assist in the discharge of fluids in the cartridge receiver tubes 24. It is the programmed application of this positive gas pressure which forces the fluid solutions to flow through the sorbent 36 and the receiver tube outlets 30, after the allotted time for the particular reaction involved has expired. Of course, where a simple rinse is used or in other situations where no fluid retention or residence is desired, the manifold 92 and 3-way valve 72 will be instructed to generate (after a short delay) a positive gas pressure for that receiver tube. The manifold 92 can also be controlled to provide a vacuum to the system to remove any inert pressurizing or drying gases used, or to exhaust gases generated by chemical reaction within the interconnection tubing and valve system of the process unit 10 at the conclusion of any particular step in the process cycle. This is accomplished through the appropriate manipulation of 3-way valve 72 and the application of a vacuum source to inlet/outlet line 26.

Before the dispensing of a fresh solution through the fluid interconnection system of the process unit 10 from multi-port valve 58 to multi-port valve 76, it is necessary to purge all wetted surfaces of the prior fluid solution. Normally, discharge of this undesired fluid within any of the fluid lines leading through 3-way valve 72 up to the input port 74 of the multi-port valve 76 is accomplished by merely positioning the central disk 82 of the second multi-port valve 76 to discharge into output port 80a. As shown, this output is connected to waste disposal line 96 and a waste receiver container (not shown) through fitting 98. The purge may be assisted through a "blow-down" of the fluid lines from the manifold 92, through the 3-way valve 72, and out through the port 80a of multi-port valve 76.

Upon the discharge of eluted fluids from the cartridge receiver tubes 24, the waste storage container 100 (contained within stand 22) is replaced with a purified sample receiver 102 having a corresponding sample container for each cartridge receiver tube location. While this change can be done manually, it is useful to have the small orifices 30 of each receiver tube 24 lead directly into a programmable dual outlet manifold 104 which, under the direction of controller 50, can discharge into either container(s) 100 or 102.

It should be understood that each of the selectable inlet ports 56a–l of the multi-port valve 58 and each of the selectable outlet ports 80a–ff of the multi-port valve 76 are programmably addressable by controller 50. By way of example, consider the connection of inlet port 56h of multi-port valve 58 (connected by tubing to the 8th container 20)) through the 3-way valve 72 to the outlet port 80q and, consequently, to the cartridge receiver tube 24 in position 17 on stand 22. This is easily accomplished by the proper addressing and control of the stepper motors 62 and 84 by controller 50, acting through signal interpreter 90, to rotate the central disks of the two multi-port valves 58, 76 to the selected input and discharge positions creating the desired fluid flowpath. This example is only one of the many different and distinct flow configurations which are possible for individually connecting each one of the containers 20 to a like, or different (smaller or larger), number of cartridge receiver tubes 24.

OPERATION OF THE SYSTEM

The following is a description of the general series of Steps which are performed in a "RANDOM" operation of the system of the present invention in which benzodiazepines are isolated and extracted from urine. For such an extraction, receiver tubes containing between about 100 and about 1000 mg (depending on sample size) of Octadecyl (C18) as solid sorbent 36 are used.

STEP 1: From the menu of possible program options as defined above, the operator selects and enters from the function keyboard 18 the choice of the "RANDOM" cycle.

STEP 2: The operator then selects and enters from the number keypad 16 the assigned number or numbers for each of the selected cartridge receiver tubes 24 to which the process solutions are to be sent.

STEP 3: Next the operator selects and enters the number of the first process container 20 to be addressed and then the amount of solution which is to be metered from said container for each of the selected cartridge receiver tubes 24.

In normal operation, the input solution selections include, in addition to introducing the sample being tested, various solutions used to pre-condition the sorbent, wash the sorbent/solute combination, elute the solute, and clean out and recondition the system before the next test cycle option is chosen and performed.

In the instant example, the solid sorbent 36 in the selected one(s) of cartridge receiver tubes 24 is pre-conditioned with a methanol wash (solution 1) and then with an 0.1M sodium carbonate solution (solution 2). An aliquot sample of each raw test sample solute/solvent solution is then placed in the cartridge receiver tubes 24 (either by independently pippetting or automatic metering from a selected container 20) and passed through the sorbent to selectively remove the solute therefrom. The extracted solute is washed to remove any residual raw solution or other contaminants remaining on the extracted solute with a mixture comprising 85 vol % 0.1M sodium carbonate/15 vol % acetonitrile (solution 3), and eluted with methanol. Prior to use, the pH of the raw solute/solvent sample materials is adjusted to about 10.5 with a pH adjusting amount of solution 2.

STEP 4: Step 3 is repeated as often as necessary to complete the final extraction, purification and elution of the desired solute.

STEP 5: The operator then starts the program, at which time the system automatically accomplishes the following:

a. the solid sorbent material is pre-conditioned with 2 aliquots of 3 ml solution 1, followed immediately by 3 ml of solution 2;
  b. 10 ml of the prepared sample solution is then passed through the sorbent in each of the selected one(s) of cartridge receiver tubes 24;
  c. the material extracted from the sample solution is then washed with two sequential 0.6 ml volumes of solution 3, said solvent being retained within the plurality of cartridge receiver tubes 24 for a sufficient amount of time to remove any impurities from the extracted solute.

In an automated system, the solutions used in Steps 5a–c would either be automatically directed to suitable waste storage containers for subsequent disposal through dual outlet manifold 104 into container 100, or manually collected and discarded. Since the volume of each solution used in this operation tends to be rather small, the hazards resulting from such temporary storage tends to be rather minimal.

Figure 6:
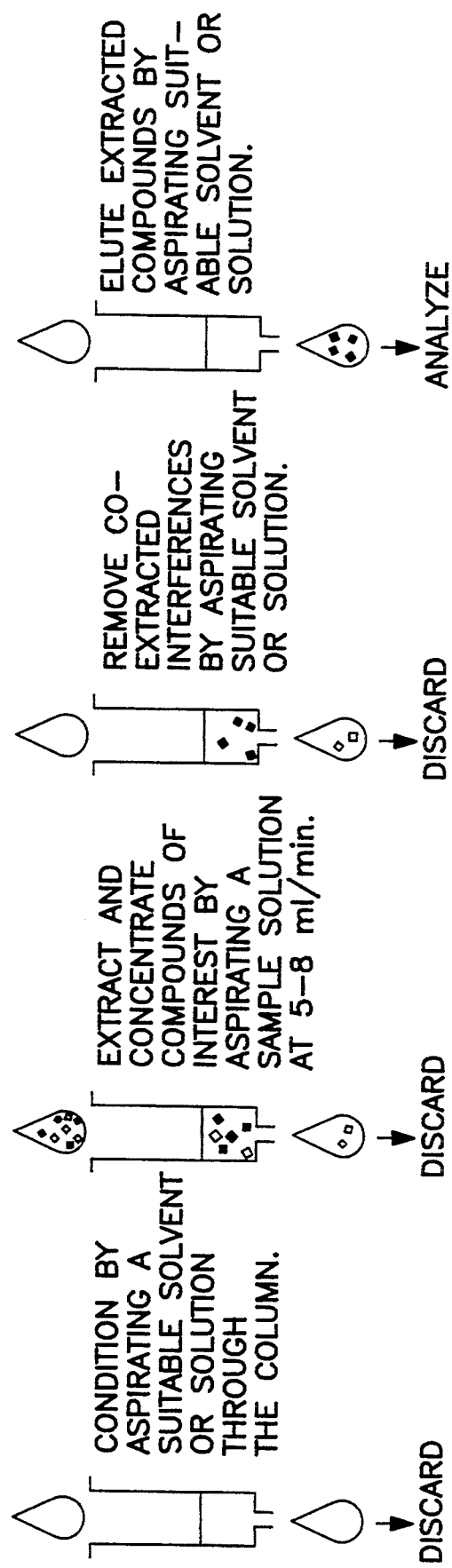
FIG. 6 is a diagrammatic representation of the general mode of using the present invention to extract a particular solute from a solution sample.

At the conclusion of Steps 5a–c, the final recovery step is accomplished by washing the extractant material with 2 sequential 0.6 ml volumes of solution 1, with the solvent being retained within the receiver tube 24 for a sufficient length of time to fully dissolve and remove the solute from solid sorbent 36. In its most basic embodiment, the system is adapted to stop at this point and emit either an aural or visual signal that the waste receiver 100 should be disconnected and replaced with the purified sample container 102 for the eluted solution. In a somewhat more advanced embodiment (illustrated in FIG. 7) the dual outlet manifold 104 can be directed by programmable controller 50 to discharge either into waste storage container 100 or into purified sample container 102, from which the final sample can be taken for analysis or other use. The general scheme of the steps described above is illustrated in FIG. 6. For the example to obtain benzodiazepines, the above procedure produces a final methanol solution suitable for immediate analysis without additional processing. For other applications, it may be necessary to evaporate the eluted solvent to either recover the solute as a solid or to reconstitute the solute in a different solvent.

Figure 7:
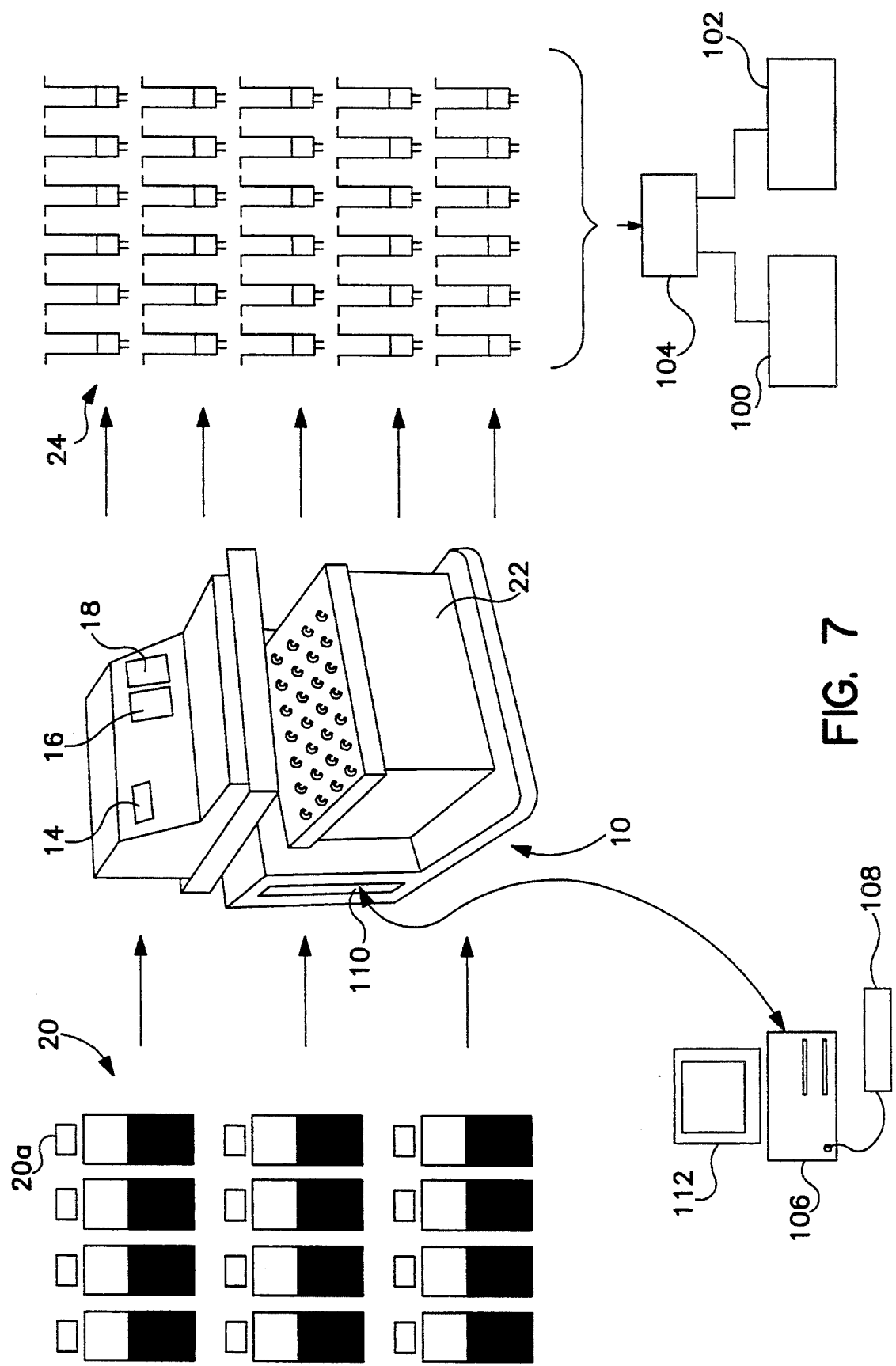
FIG. 7 is a simplified diagrammatic representation showing an alternative embodiment of the principal external features of the present invention.

In an alternative embodiment, as shown in FIG. 7, controller 50 comprises a computer 106 having as an integral part thereof an associated programmable read-only-memory (PROM) to assume control, in combination with a central processing unit, over the various functions of the operable elements of system 10. Monitoring and control of these elements is accomplished through a set of fixed parameters contained within the PROM operating in conjunction with a set of instructions supplied by the system operator through the computer keyboard 108. These pre-programmed PROM factors include such items as the quantity of fluid per pulse applied to solenoid drive 66 and, therefore, the total number of pulses required to extract and meter a selected quantity of fluid from a selected one of solution containers 20, the number of pulses required to move the central disks of the two multi-port valves in the system to move from one inlet (or outlet) port to the next available position, the solute hold time within a selected cartridge receiver tube 24 for each given procedure, and the "blow-down" time for clearing the device of fluid after a given procedure is completed.

Communication between system 10 and the computer 106 is through an integral RS232 communications port 110 and device status and other information as needed are displayed on a video monitor 112. This combination not only provides a versatile alternative to alphanumeric display 14 and keypads 16 and 18 but allows the system operating instructions to be setup, monitored, modified and controlled from a central or remote location. Other capabilities available to the system operator are those of creating new procedures when required, changing the default parameters stored in the PROM for a given procedure, changing the report options and aborting the program at the operator's option.

Typically, the options and procedures are presented in menu form, thus allowing the easy selection of operations such as the number of aliquots desired, the flow rate of each solution used, the hold time after a solution dispensing operation is completed, and the gas dry time which the operator desires to have performed. Further, the software used provides the ability to enter a number of record keeping items such as the title of the overall operation being performed, e.g "STEROIDS FROM URINE" or "PCB's FROM WATER," and the identification of each of the receiver cartridges 24, and of the sorbent material 36 used. These capabilities are especially valuable when toxic, flammable, radioactive or otherwise hazardous materials are involved, or a plurality of operating systems must be controlled.

To facilitate this overall control, the process unit 10 may further comprise position indicators such as one or more position encoders incorporated onto multi-port valves 58 and 76. The position encoders provide a unique signal which identifies each input or output connection point. Also, there can be incorporated with each of these valves a position sensor to establish an exact position for the rotating central disk sections of the multi-port valves at the start of a given procedure. This is required since, usually, each "step" of the motors 62 and 84 requires more than one step pulse to move the inlet (outlet) from one "flow-through" position to another. The sensor may be a photo-illumination and detection pair placed on the periphery of the rotor and stator units of the valves.

In one mode of operation, at the start of operation, the sensors respond to a position inquiry from the computer by causing both of the valve rotors to move to an initial starting point, or "home" position, which is established when the photo-illuminator and detector line up. At the start of a given procedure, once this starting position has been reached, the computer 106 provides a signal to restart motor drive 62 and the number and polarity of the pulses required to cause the central rotor of valve 58 to move from this "home" position to the first fluid input location and establish the fluid flowpath for the selection. Thereafter, the computer monitors the position of the motor driven rotor by keeping track of the number of pulses generated to move the rotor to its present position. Where more than one process solution is to be used, it computes and then, at the proper time, transmits the number and polarity of the steps needed to move the central rotor forward to the next selected solution container location. Similar signals are sent to initially position and then move the second multi-port valve motor 84.

In an alternative embodiment, home positioning of the valve rotors is assumed at the conclusion of a test run by having the position signal interpreter 90 count down to zero from whatever number represents the final operational positions of the valve rotors. This would move the motor driven rotors back to "home," which, typically, is at an open inlet on valve 58 or position 80ff on valve 76.

The control signals sent to solenoid drive 66 come directly from controller 50 and give the number of pulses required to cause the pump to withdraw the desired amount of fluid from the selected sample container 20 and then pump it into the system. For this operation, no prepositioning of a rotatable member is required.

At the start of operation, the computer 106 also polls each of the receiver cartridge tube locations to detect the presence or absence of a cartridge tube at each output location. The absence of a "cartridge present" signal from the cartridge sensing means associated with each of the valves connected to outlet nozzles 32 will cause the computer to permanently "lock-off" that position so that no fluid can be pumped thereto. This lock will remain in effect so long as no cartridge receiver tube 24 is placed and detected at that position and will supersede an operator's instruction to the contrary.

The control and status of all operating devices are polled and controlled by the computer 106 through a standard interface using digital-to-analog and analog-to-digital signal conversion and standard communication techniques. Once a procedure is started, the computer controls the starting position, movement and final positions of both rotary valves 58, 76, the pumping time of pump assembly 64, the actuation and positioning of 3-way valve 72, the generation and release of gas pressures, blow down and/or venting of the system, etc. and all other operating and condition features of the present invention. With this degree of control, it is now possible to individually control or "batch" process each of the receiver cartridge tubes 24 so that set up and performance of a variety of different fluid treatment processes is easily accomplished.

A basic display screen as used in conjunction with monitor 112 is shown in FIG. 8. This provides the system operator with a degree of flexible system control and management not possible with the sequenced instruction dependent alpha-numeric display and keypads used with the basic embodiment described above. For example, the computer 106 and accompanying screens viewable on the monitor 112 give the operator the power to alter or modify one or a number of control parameters applicable to a given portion (or all) of a particular test procedure, with the operating system defaulting to the test parameter instructions in the PROM only if no further entry is made. The monitor 112 also displays the status of each step in the operational procedure selected, and provides the ability to better identify test samples by requiring unique identification means on each of the cartridge receiver tubes 24 and then reading these unique cartridge receiver tube identifiers from each of the individual tubes (in the form of "bar-codes") with a light wand (or other "bar-code" reader means) as they are placed at a particular position on stand 22. At the conclusion of the operating procedure, the monitor 112 provides the operator a summary of the amounts and types of test solutions used for inventory control. Display screens showing an example procedure involving one methanol conditioning, one water wash and two NaOH elution cycles are shown in FIGS. 9a-d. Lastly, a display screen giving the locations of the solution containers 20 containing these solutions is presented as FIG. 10. The computer 106 also permits reports of the solid phase extraction and elution procedure to be printed on an associated printer for retention with the actual test samples.

It will be understood that various changes in the details, materials, and arrangement of the parts which have been described and illustrated in order to explain the nature of the invention, may be made by those skilled in the art without departing from the spirit and principles of the invention, and accordingly, reference should be made to appended claims, rather than to the foregoing specification, as indicating the scope of the invention.

What is claimed is:

1. A method for extracting one or more particular solutes from a sample solution, said method comprising the steps of:
   a. placing an amount of said sample solution into a non-contaminating receptacle, said receptacle being operatively connected to means adapted to meter predetermined amounts of said solution therefrom;
   b. programmably introducing at least one metered amount of said sample solution into a selected one or more of a plurality of cartridge receiver tubes, each of said selected receiver tubes containing an amount of the same or a different solid phase extractant or sorbent through which said solution will pass, said sorbent being selected to remove substantially all of one of said particular solutes from said sample solution;
   c. programmably introducing into said selected receiver tubes a predetermined amount of one or more solvents to pass through said sorbent, said solvents being adapted to selectively dissolve and remove substantially all of any residual sample solution and residual contaminants remaining on or absorbed by said sorbent while permitting substantially all of said particular solute to remain;
   d. programmably introducing into said selected receiver tubes one or more predetermined amounts of at least one solvent to pass through said sorbent and selectively form a contamination-free solution with a selected one of said particular solutes resident therein; and
   e. removing said contamination-free solution from said selected receiver tubes for further use.

2. The method of claim 1 wherein the sequential order and amounts of said metered solutions are controlled by a programmable control means.

3. The method of claim 1 wherein the steps of sequentially introducing selected solutions is controlled by a programmable selection means and the quantitative transfer of said solutions is performed by programmable pump means and valve means.

4. The method of claim 1 further comprising the step of introducing into said receiver tubes and passing through said sorbent an amount of one or more conditioning solutions before the introduction of the sample solution into the receiver tubes.

5. The method of claim 1 further comprising the step of flushing the fluid connection between a plurality of inlet ports of a first multi-port valve means and individual stop valves connected to each of the plurality of outlet ports of a second multi-port valve means which connect the sample receptacle and selected solution receptacles to the plurality of cartridge receiver tubes to remove any contaminants from solution residues.

6. The method of claim 1 further comprising the step of drying the fluid connection between a plurality of inlet ports of a first multi-port valve means and individual stop valves connected to each of the plurality of outlet ports of a second multi-port valve means which connect the sample receptacle and selected solution receptacles to the plurality of cartridge receiver tubes to remove any contaminants from solution residues.

7. A method for extracting one or more particular solutes from a sample solution, said method comprising the steps of:
 a. placing an amount of said sample solution into at least a selected one of a plurality of cartridge receiver tubes, each of said receiver tubes containing an amount of the same or a different solid phase extractant or sorbent through which said solution will pass, said sorbent being selected to remove substantially all of one of said particular solutes from said sample solution;
 b. programmably introducing into said selected receiver tubes a predetermined amount of one or more solvents to pass through said sorbent, said solvents being adapted to selectively dissolve and remove substantially all of any residual solution and residual contaminants remaining on or absorbed by said sorbent while permitting substantially all of said particular solute to remain;
 c. programmably introducing into said selected receiver tubes one or more predetermined amounts of at least one solvent to pass through said sorbent and selectively form a contamination-free solution with a selected one of said particular solute resident therein; and
 d. removing said contamination-free solution from said selected receiver tubes for further use.

8. The method of claim 7 wherein the sequential order and amounts of said metered solutions are controlled by a programmable control means.

9. The method of claim 7 wherein the steps of sequentially introducing selected solutions is controlled by a programmable selection means and the quantitative transfer of said solutions is performed by programmable pump means and valve means.

10. The method of claim 7 further comprising the step of introducing into said receiver tubes and passing through said sorbent an amount of one or more conditioning solutions before the introduction of the sample solution into the receiver tubes.

11. The method of claim 7 further comprising the step of flushing the fluid connection between a plurality of inlet ports of a first multi-port valve means and individual stop valves connected to each of the plurality of outlet ports of a second multi-port valve means which connect the sample receptacle and selected solution receptacles to the plurality of cartridge receiver tubes to remove any contaminants from solution residues.

12. The method of claim 7 further comprising the step of drying the fluid connection between a plurality of inlet ports of a first multi-port valve means and individual stop valves connected to each of the plurality of outlet ports of a second multi-port valve means which connect the sample receptacle and selected solution receptacles to the plurality of cartridge receiver tubes to remove any contaminants from solution residues.

* * * * *